United States Patent [19]

Adachi et al.

[11] Patent Number: 5,919,644
[45] Date of Patent: Jul. 6, 1999

[54] METHOD FOR ASSAYING SULFATE-CONJUGATED BILE ACID AND THEREFORE

[75] Inventors: Kenichi Adachi, Uji; Yasuhiko Tazuke, Ashiya; Yoji Tsukada, Kyoto, all of Japan

[73] Assignee: Marukin Shoyu Co., Ltd., Kagawa, Japan

[21] Appl. No.: 08/875,983

[22] PCT Filed: Dec. 17, 1996

[86] PCT No.: PCT/JP96/03678

§ 371 Date: Aug. 21, 1997

§ 102(e) Date: Aug. 21, 1997

[87] PCT Pub. No.: WO97/23643

PCT Pub. Date: Jul. 3, 1997

[30] Foreign Application Priority Data

Dec. 21, 1995 [JP] Japan ................................. 7-333336

[51] Int. Cl.⁶ ........................................................ C12Q 1/32
[52] U.S. Cl. ............................... 435/26; 435/25; 435/810
[58] Field of Search ................................... 435/4, 25, 26, 435/18, 810; 436/904

[56] References Cited

U.S. PATENT DOCUMENTS 5,091,305  2/1992  Sugimori et al. .......................... 435/19
5,100,795  3/1992  Sugimori et al. ........................ 435/196

FOREIGN PATENT DOCUMENTS 56-61367  5/1981  Japan.
2-145183  6/1990  Japan.

OTHER PUBLICATIONS

Ishiyama M., A New Sulfonated Tetrazolium Salt That Produces a HighlyWater Soluble Formazan Dye, Chem Pharm Bull 41(6) 1118–1122, 1993.
Chem. Pharm. Bull., vol. 41, No. 6 (1993) pp. 1118–1122, M. Ishiyama et al.

*Primary Examiner*—Ralph Gitomer
*Attorney, Agent, or Firm*—Knobbe, Martens, Olson & Bear, LLP

[57] ABSTRACT

In a method of quantifying sulfate-conjugated bile acid in a sample with bile acid sulfate sulfatase and a reductive system indicator, an 2-(4-iodophenyl)-3-(4-nitrophenyl)-5-(2,4-disulfophenyl)-2H-tetrazolium salt is used as a reductive system indicator. Sulfate-conjugated bile acid can be quantified through a single reaction without complication.

10 Claims, 14 Drawing Sheets

METHOD FOR ASSAYING SULFATE-CONJUGATED BILE ACID AND THEREFORE

This is a 35 U.S.C. § 371 application of PCT/JP96/03678 filed Dec. 17, 1996.

FIELD OF THE INVENTION

The present invention relates to a method of quantitatively determining sulfate-conjugated bile acid and a kit for determining sulfate-conjugated bile acid. The kit of the invention is particularly useful in the diagnosis of hepatobiliary diseases.

BACKGROUND OF THE INVENTION

It is well known that the bile acid in blood markedly increases due to hepatobiliary diseases. It is therefore an important item to determine the bile acid in blood for evaluating the hepatic function in clinical examinations. It has been clarified that the kinetics of bile acid in urine is similar to that of bile acid in blood. In urine, however, a large proportion of bile acid occurs as a sulfate-conjugated form (sulfate ester, at the 3-position hydroxyl group, of bile acid), which is highly soluble in water, hence the assay of bile acid is not easy.

The present inventors previously developed an enzyme capable of efficiently hydrolyzing the 3α-position sulfate ester moiety of sulfate-conjugated bile acid, namely bile acid sulfate sulfatase (BSS), and established a method capable of determining the sulfate-conjugated bile acid in biological samples in a simple and easy manner by the enzymatic method using said enzyme as the principal reagent (Japanese Unexamined Patent Publication (Kokai) No.145183/1990).

Subsequently, it was revealed that assaying of urinary sulfate-conjugated bile acid by the above method, as a method for diagnosing of hepatobiliary diseases, is comparable in diagnostic efficiency to blood chemistry test for GOT, GPT, Y-GTP, TBA and so on and that said method is useful as a method of noninvasive liver function test via urine [Kan Tan Sui (Liver, Gallbladder, Pancreas), volume 31 (1995), No. 2, pp. 315–326].

The assay principle of this prior art method consists in that sulfate-conjugated bile acid is first converted, under the action of BSS, to 3β-hydroxybile acid, the latter is treated with β-hydroxysteroid dehydrogenase (β-HSD) in the presence of nicotinamide adenine dinucleotide (NAD), which is a coenzyme of said β-HSD, and the NADH produced together with 3-oxobile acid is colorimetrically assayed using Nitrotetrazolium Blue (NTB), which is a reductive system indicator generally used as a high sensitive indicator for NADH. When viewed as a clinical test method, however, this method is still unsatisfactory from the viewpoint that a great number of clinical samples should be assayed rapidly without great labor.

Thus, this method, which is directed to urine samples, results in a great irregularity among urine samples as compared with serum samples, with a continuous increase in blank value, which of the extend is also various among urine samples, due to endogenous color developing substances in urine samples. To eliminate the blank value from each assay value, it is therefore inevitable to additionally perform assaying using a blank reagent without BSS. Thus, it is necessary to perform two assays (i.e. sample and blank assays) in parallel for each sample; this makes the procedure complicated. Furthermore, the reductive system indicator Nitrotetrazolium Blue (NTB) and the formazan thereof are scarcely soluble in water, leading to contamination of cells for colorimetry after one use. For repeated use, the cuvettes have to be washed very carefully, and this makes it difficult to apply the method to automated analyzers. Under the present circumstances, therefore, said method has to be performed manually, which places restrictions on the number of samples that can be treated and from the viewpoint of time, among others.

Accordingly, it is an object of the present invention to provide a method for assaying sulfate-conjugated bile acid and a kit therefor, which are suited for application to automated analyzers in general use.

DISCLOSURE OF THE INVENTION

The present inventors made intensive investigations to find out an analytical reagent for automated analyzers which satisfies the conditions (1) that it enables elimination of the blank value of sample in a single assay reaction system, (2) that the overall reaction can be completed in a short time and (3) that it produces no apparatus contamination problem and enables assaying with high sensitivity.

In the course of their study, the inventors tentatively used, in lieu of NTB (hereinafter referred to as "Comparative reagent a"),

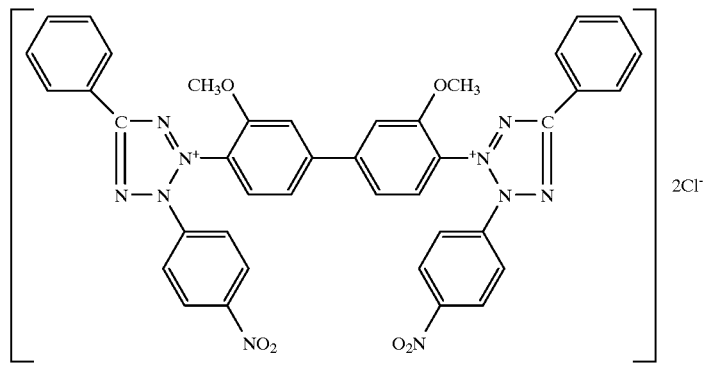

various water-soluble reductive system indicators, for example 2-(4-iodophenyl)-3-(2,4-dinitrophenyl)-5-(2,4-disulfophenyl)-2H-tetrazolium monosodium salt (hereinafter referred to as "Comparative reagent b"),

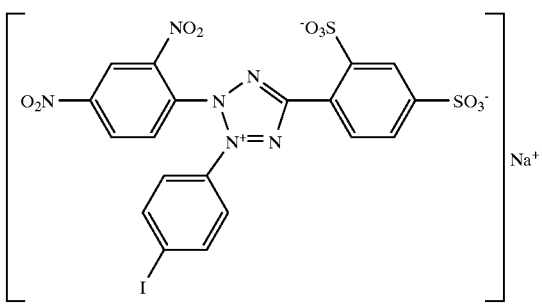

and 2-benzothiazolyl-3-(4-carboxy-2-methoxyphenyl)-5-[4-(2-sulfoethylcarbamoyl)phenyl]-2H-tetrazolium salt (hereinafter referred to as "Comparative reagent c").

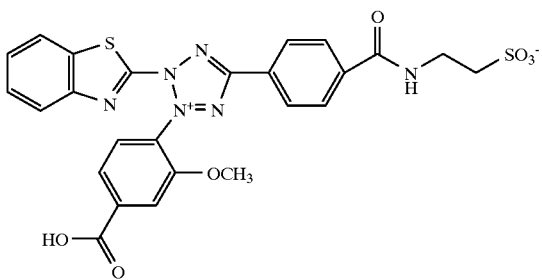

Even when such reagents were used, however, the influence of color developing substances in urine was too strong to stabilize the blank value of sample, hence said reagents were unsuited for automation purposes, failing to achieve the object of the present invention.

In a further study, however, the present inventors found that the above object can be attained for the first time by using an 2-(4-iodophenyl)-3-(4nitrophenyl)-5-(2,4-disulfophenyl)-2H-tetrazolium salt (hereinafter sometimes referred to as "reductive system indicator of the invention")

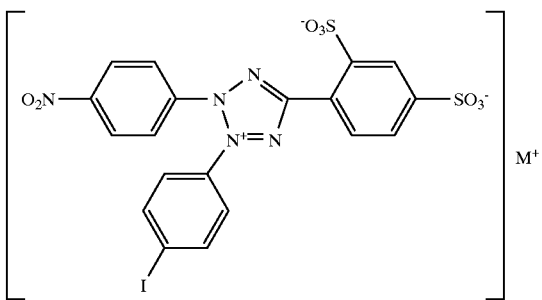

wherein $M^+$ represents an alkali metal ion or an alkaline earth metal ion, and thereby completed the invention.

Thus, the finding of the present inventors is that, among reductive system color forming tetrazolium salt reagents, said 2-(4-iodophenyl)-3-(4-nitrophenyl)-5(2,4-disulfophenyl)-2H-tetrazolium salt is influenced only to a very slight extent by endogenous color developing substances in urine or blood, said extent being within tolerance limits. In accordance with the method and kit of the present invention using said reagent as indicator, it is possible to determine the sulfate-conjugated bile acid in the sample using a single cuvette. Said method comprises causing the indicator contained in the first reagent to act on a sample in order to react an endogenous color developing substance in the sample, as blank color development reaction, then measuring the resulting absorbance as the blank value, and causing a BSS contained in the second reagent to act on the sample, then measuring the absorbance resulting from the color development reaction due to the desulfation product derived from sulfate-conjugated bile acid, followed by determining the sulfate-conjugated bile acid in the sample based on the difference between the former absorbance and the latter abosorbance.

Said 2-(4-iodophenyl)-3-(4-nitrophenyl)-5-(2,4-disulfophenyl)-2H-tetrazolium salt and the formazan thereof are soluble in water, hence cuvettes contaminated by the reagent can be easily cleaned up and no apparatus contamination problem arises. In addition, the molar extinction coefficient of the formazan of said reagent is as high as $\epsilon=3.7 \times 10^4$ ($\lambda=438$ nm). Therefore, the reagent enables high sensitivity assays.

To sum up, the present invention provides a method for assaying sulfate-conjugated bile acid using bile acid sulfate sulfatase (BSS) and a reductive system indicator wherein said reductive system indicator is an 2-(4-iodophenyl)-3-(4-nitrophenyl)-5-(2,4-disulfophenyl)-2H-tetrazolium salt, as well as an assay kit therefor.

More detailedly, the invention provides an assay method which comprises (1) causing BSS to act on a sample, (2) then causing β-hydroxysteroid dehydrogenase (β-HSD) to act on the resulting 3β-hydroxybile acid in the presence of nicotinamide adenine dinucleotide (NAD) and (3) causing an electron carrier and an 2-(4-iodophenyl)-3-(4-nitrophenyl)-5-(2,4-disulfophenyl)-2H-tetrazolium salt to act on NADH formed simultaneously with 3-oxobile acid, followed by assaying the thus-formed formazan.

The kit provided by the present invention for assaying sulfate-conjugated bile acid comprises a first reagent comprising β-HSD, NAD, an electron carrier and an 2-(4-iodophenyl)-3-(4-nitrophenyl)-5-(2,4-disulfophenyl)-2H-tetrazolium salt, and a second reagent comprising BSS.

The present inventors further found that when 3oxo-5β-steroid-$\Delta^4$-dehydrogenase ($\Delta^4$-DH), a dehydrogenase acting on 3-oxobile acid which is the product formed by the action of β-HSD, is used together with ingredients in the first reagent mentioned above, the 2-(4-iodophenyl)-3-(4-nitrophenyl)-5-(2,4-disulfophenyl)-2H-tetrazolium salt reacts as an acceptor for $H^+$ resulting from the dehydrogenation, giving one more formazan molecule, whereby the absorbance value is nearly doubled, hence, as compared with the prior art, the assay sensitivity increases about twofold.

Thus, the present invention further provides an assay method as mentioned above, wherein the formazan formed and determined in step (3) is the sum total of (i) the formazan formed by the reaction of the electron carrier and the 2-(4-iodophenyl)-3-(4-nitrophenyl)-5-(2,4-disulfophenyl)-2H-tetrazolium salt with NADH formed simultaneously with 3-oxobile acid and (ii) the formazan formed by the reaction of $\Delta^4$-DH and the 2-(4-iodophenyl)-3-(4-nitrophenyl)-5-(2,4-disulfophenyl)-2H-tetrazolium salt with 3-oxobile acid, as well as a kit as mentioned above wherein the first reagent comprises β-HSD, NAD, an electron carrier, $\Delta^4$-DH and an 2-(4-iodophenyl)-3-(4-nitrophenyl)-5-(2,4-disulfophenyl)-2H-tetrazolium salt.

The assay method and kit above mentioned result in reducing of the sample volume, decreasing of the influence of contaminants in the sample, and providing of more precise values, due to the increasing assay sensitivity.

By using the assay method and kit, it is possible to quantitatively determine sulfate-conjugated bile acid in urine or blood.

The electron carrier to be used in the above assay method and kit is a substance catalyzing the reaction consisting in electron transfer from an electron donor to an electron acceptor.

The 2-(4-iodophenyl)-3-(4-nitrophenyl)-5-(2,4-disulfophenyl)-2H-tetrazolium salt, which is the reductive system indicator of the invention, is a known substance and is readily available on the market. As the salt thereof, there may be mentioned alkali metal salts such as the sodium, potassium and lithium salts and alkaline earth metal salts such as the magnesium and calcium salts, among others. Thus, for example, the monosodium salt available from Dojindo Laboratories under the designation WST-1 can be used.

The enzymes BSS, β-HSD and $\Delta^4$-DH to be used in the present invention are known substances and may be of any organism origin; for example, each may suitably be of the *Pseudomonas testosteroni* origin. Genetically engineered products may also be used.

BSS can be purified as described in the literature, for example Y. Tazuke, K. Matsuda, K. Adachi, & Y. Tsukada: Biosci. Biotech. Biochem., 58, 889–894 (1994).

β-HSD can be purified as described in the literature, for example Richard M. Schultz, Ernest V. Groman and Lewis L. Engel: J. Biol. Chem., 252, 3775–3783 (1977). It is also possible to use a commercial product available from Sigma Chemical Co., for instance.

$\Delta^4$-DH can be purified as described in the literature, for example S. J. Davidson & P. Talalay: J. Biol. Chem., 241, 906–915 (1966).

NAD to be used in the present invention may be a commercial product, for instance.

The electron carrier to be used in the present invention is, for example, an enzyme such as diaphorase or NADH oxidase, or such a substance as phenazine methosulfate (PMS), 1-methoxyphenazinium methylsulfate (1-methoxy-PMS) or 9-dimethylaminobenzo-α-phenazoxonium chloride (Meldola's Blue). One or more of these may be used. At least one member selected from the group consisting of diaphorase, 1-methoxyphenazinium methylsulfate and 9-dimethylaminobenzo-α-phenazoxonium chloride is preferred. These electron carriers may be commercial products. Thus, for example, diaphorase is available from Oriental Yeast Co., Ltd. and 1-methoxy-PMS and Meldola's Blue are available from Dojindo Laboratories; each product can be used.

In the following, the method of the present invention is described in reference to FIG. 1 and FIG. 2.

Referring to FIG. 1, the first reaction is allowed to proceed in a cuvette placed on an automated analyzer and containing a sample, for example urine or blood, by causing the first reagent containing NAD, β-HSD, an electron carrier and an 2-(4-iodophenyl)-3-(4-nitrophenyl)-5-(2,4-disulfophenyl)-2H-tetrazolium salt to act on endogenous color developing substances occurring in the sample for a certain period of time for color development, and the blank value (in FIG. 1, measured value A) is determined. The time required is about 5 minutes.

Then, the second reaction is allowed to proceed in the same cuvette by adding thereto the second reagent containing BSS to thereby converting sulfate-conjugated bile acid in the sample to 3β-hydoxybile acid, said 3β-hydoxybile acid is oxidized by β-HSD in the cuvette and the coproduct NADH causes color development. After a certain period of time, the absorbance is measured (measured value B). The time required is about 2 to 5 minutes. Based on the value obtained by substrating the blank value (measured value A) from the measured value B, the sulfate-conjugated bile acid level in the sample, which is to be known, is calculated.

Further, as shown in FIG. 2, when $\Delta^4$-DH, a dehydrogenase acting on 3-oxobile acid formed under the action of β-HSD, is used together with NAD, β-HSD, an electron carrier and 2-(4-iodophenyl)-3-(4-nitrophenyl)-5-(2,4-disulfophenyl)-2H-tetrazolium salt, said tetrazolium salt reacts as an acceptor for H$^+$ resulting from the dehydrogenation, whereby one more formazan molecule is formed, with the result that the absorbance is nearly doubled, hence the assay sensitivity can be nearly doubled as compared with the prior art methods.

Thus, the first reaction is allowed to proceed in a cuvette placed on an automated analyzer by causing the first reagent containing NAD, β-HSD, $\Delta^4$-DH, an electron carrier and an 2-(4-iodophenyl)-3-(4-nitrophenyl)-5-(2,4-disulfophenyl)-2H-tetrazolium salt to act on endogenous color developing substances in a sample, for example urine or blood, for a certain period of time for color development, and the blank value (in FIG. 1, measured value A) is determined. The time required is about 5 minutes.

Then, the second reaction is allowed to proceed in the same cuvette by adding thereto the second reagent containing BSS, whereby sulfate-conjugated bile acid contained in the sample is converted to 3β-hydroxybile acid, said 3β-hydroxybile acid is oxidized under the action of β-HSD present in the cuvette and the simultaneous formed products NADH and 3-oxobile acid react with the electron carrier and the reductive system indicator of the invention and with $\Delta^4$-DH and the reductive system indicator of the invention, respectively, leading to color development. After a certain period of time following the addition of the second reagent, the absorbance is measured (measured value B). The time required is about 2 to 5 minutes. Based on the value obtained by substrating the blank value (measured value A) from the measured value B, the sulfate-conjugated bile acid level in the sample, which is to be known, is calculated.

The principle of the present method for assaying sulfate-conjugated bile acid in samples is as mentioned above. The present method bases on the finding that when an 2-(4-iodophenyl)-3-(4-nitrophenyl)-5-(2,4-disulfophenyl)-2H-tetrazolium salt is used as the indicator in colorimetric determination of the resulting NADH (and 3-oxobile acid), it becomes for the first time possible to eliminate the sample blank in a single assay system.

The sample volume can be selected arbitrarily.

In particular, when the sample is urine, the effect is remarkable.

The kit is as follows. The first reagent basically comprises βHSD, NAD, an electron carrier and an 2-(4-iodophenyl)-3-(4-nitrophenyl)-5-(2,4-disulfophenyl)-2H-tetrazolium salt (reductive system indicator of the invention). For doubling the sensitivity, the first reagent may contain $\Delta^4$-DH as well. The second reagent basically comprises BSS.

In addition to the above ingredients, a surfactant, ascorbate oxidase (ASOD) and/or a buffer may be contained in the first and/or the second reagent for reaction promotion and for elimination of influences of interfering substances.

Further, for stabilizing the enzymes mentioned above, a saccharide such as sorbitol, mannitol, glycerol, saccharose or trehalose, serum albumin or the like may be added to the first and/or the second reagent. It is also possible to incorporate therein ethylenediaminetetraacetic acid (EDTA), sodium azide and/or oxamic acid.

The first and the second reagents may be in the form of powders (lyophilizates) to be reconstituted by addition of a buffer solution or water on the occasion of use or in the form of solutions. The buffer solution or water to be added may be included as a reagent in the kit.

A reagent containing sulfate-conjugated bile acid (preferably glycolithocholic acid-3-sulfate or the like) serving as a standard substance may be included, as a reagent, in the kit. The concentration thereof in the standard solution is not critical but recommendably is, for example, about 10 $\mu$M to 100 $\mu$M. This reagent may be in the form of a powder (lyophilizate) to be reconstituted by adding a buffer solution or water on the occasion of use or in the form of a solution. The buffer solution or water to be added may be included in the present kit.

One or more other reagents generally used in kits of this kind may further be included as reagents in the kit.

The ingredients in these reagents each is contained in the kit in its effective amount. The effective amounts of the respective ingredients can be fixed with ease by those skilled in the art. Specific examples are as follows.

The ingredients can be used in the following respective final concentration ranges in the reaction mixture resulting from addition of the first and the second reagents to the sample:

β-HSD 100 to 1,000 U/L
NAD 0.3 to 5 g/L
Reductive system indicator of the invention
   0.1 to 2 g/L
$\Delta^4$-DH 100 to 3,000 U/L The concentration of the electron carrier in the first reagent is not critical provided that it is sufficient for electron transfer from NADH in the reaction mixture. In the case of diaphorase, for instance, it can be used in the range of 1,000 to 20,000 U/L and, in the case of 1-methoxy-PMS or Meldola's Blue, in the range of 0.01 to 0.5 mM. For other electron carriers, their concentrations can be determined with reference to these values.

The concentration of BSS contained in the second reagent, when in the above reaction mixture, is about 100 to 3,000 U/L.

The concentrations of the respective ingredients mentioned above are preferably in the following ranges:

β-HSD 200 to 500 U/L
NAD 0.4 to 1 g/L
Reductive system indicator of the invention
   0.2 to 0.5 g/L
Electron carrier
   Diaphorase 2,000 to 10,000 U/L
   1-Methoxy-PMS or Meldola's Blue
     0.03 to 0.05 mM
$\Delta^4$-DH 300 to 1,000 U/L
BSS 200 to 500 U/L.

As the buffer, use can be made of Good's buffers, more specifically HEPES, MOPS, TAPS, HEPPSO, TES, TAPSO, POPSO, EPPS, PIPES and the like. The concentration thereof in the reaction mixture is recommendably such that 50 to 200 mM Good's buffer with a pH of 7 to 8 is provided. These may be incorporated in the first and/or the second reagent and may be reconstituted by addition of water on the occasion of use to give the above concentration, or be added in the form of a buffer solution to the reaction mixture on the occasion of preparation thereof, to give the above concentration. The water or buffer solution to be added may be included, as a reagent, in the kit.

ASOD may be contained in the reaction mixture in a concentration of 50 to 500 U/L, preferably 50 to 200 U/L.

Surfactant species which can be contained are Tween type surfactants, among others. Typically, Tween 20 may be contained in the reaction mixture in a concentration of 0.2 to 1.5% by weight.

Other ingredients which may be incorporated can be contained in respective appropriate concentrations.

A typical embodiment of the method of the present invention is as follows. In the case of a urine sample, for instance, the first reagent is admixed with 10 to 20 $\mu$l of the sample and, after continuedly allowing the reaction to proceed at 37° C. for a certain period (e.g. about 5 minutes), the absorbance is read and used as the blank value. Then, the second reagent is admixed with the above mixture and, after continuedly allowing the reaction to proceed for a certain period (e.g. 2 to 5 minutes), the absorbance is read. The blank value is subtracted from this value to give the increment in absorbance attained. The sulfate-conjugated bile acid level in the urine sample can be calculated by comparing with a standard value which is the increment in absorbance obtained by using a standard solution containing a standard substance and proceeding in the same manner.

In the case of blood, too, assaying can be performed in the same manner as mentioned above.

In accordance with the present invention, sulfate-conjugated bile acid can be quantitatively determined in a single reaction system using an automated analyzer generally used for clinical examinations, with markedly improved assay operability. The assay is possible using an automated analyzer without requiring much labor. The assay treatment performance of samples can be improved as well.

BEST MODES FOR CARRYING OUT THE INVENTION

The following examples illustrate the invention in further detail. They are, however, by no means limitative of the scope of the present invention. Hereinafter, unless otherwise specified, "%" means "% by weight".

COMPARATIVE EXAMPLE 1

Figure 1A:
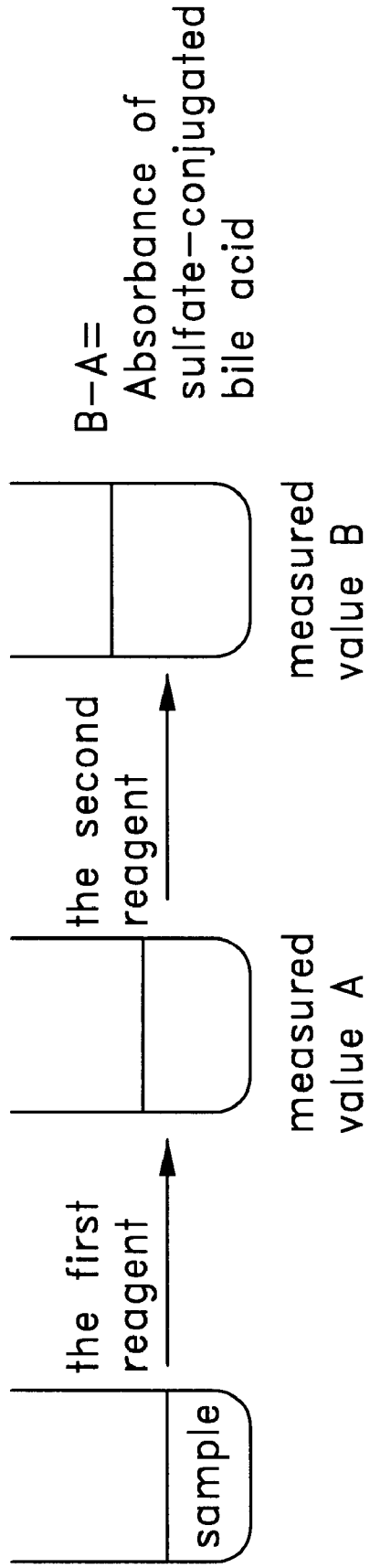
FIG. 1 illustrates the method of the present invention and the prior art method.
Figure 1B:
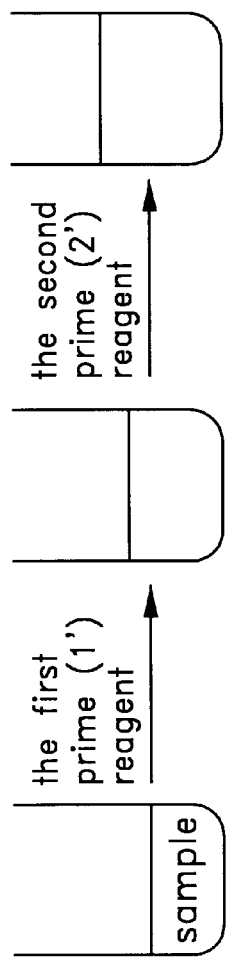
Figure 1B:
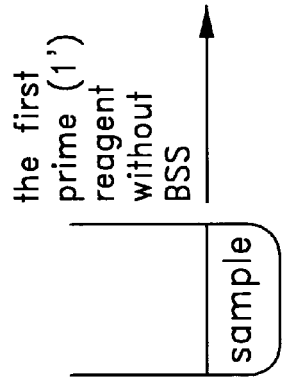
Figure 2A:
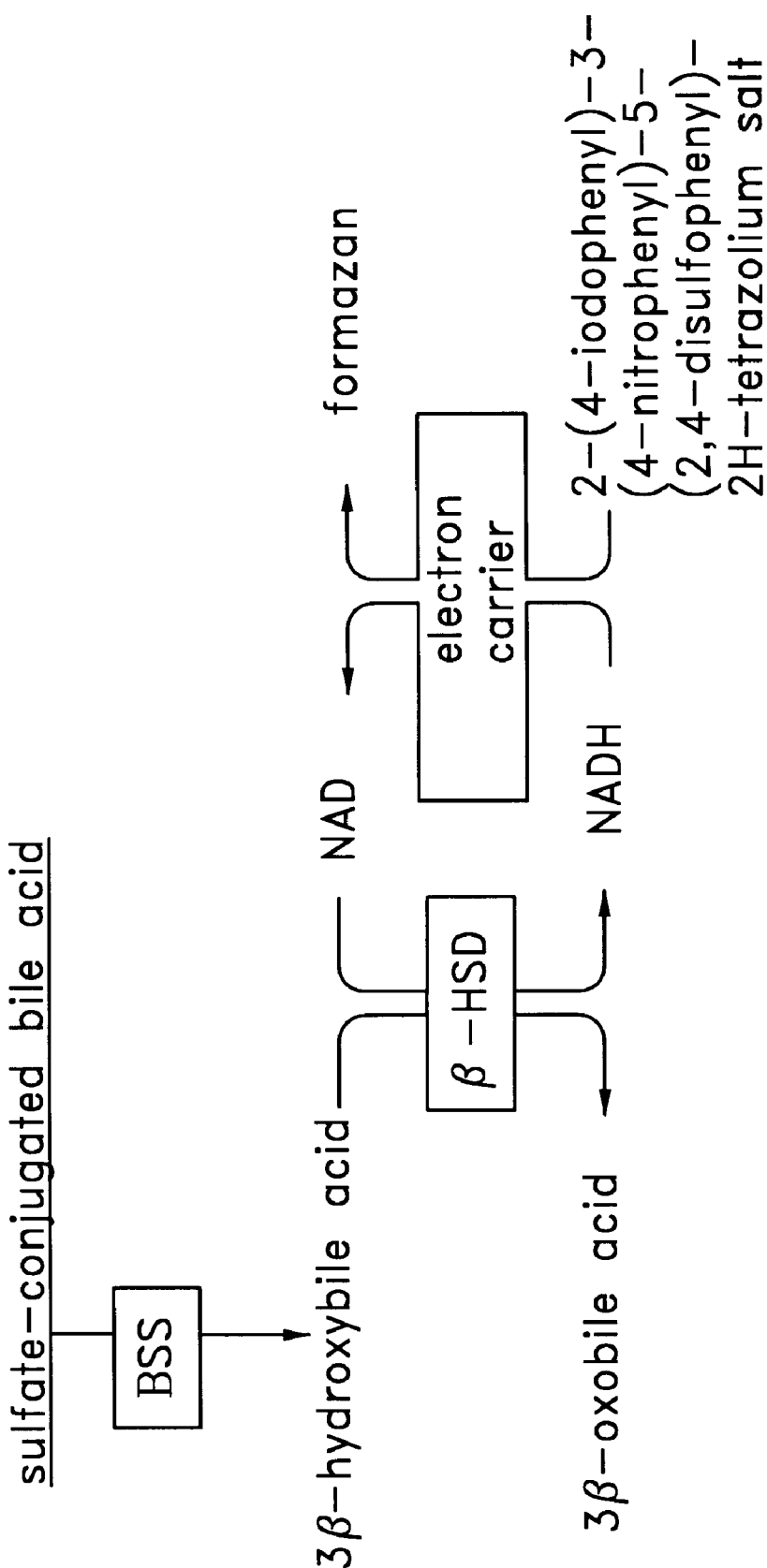
FIG. 2 illustrates the principle of the method of the present invention.
Figure 2B:
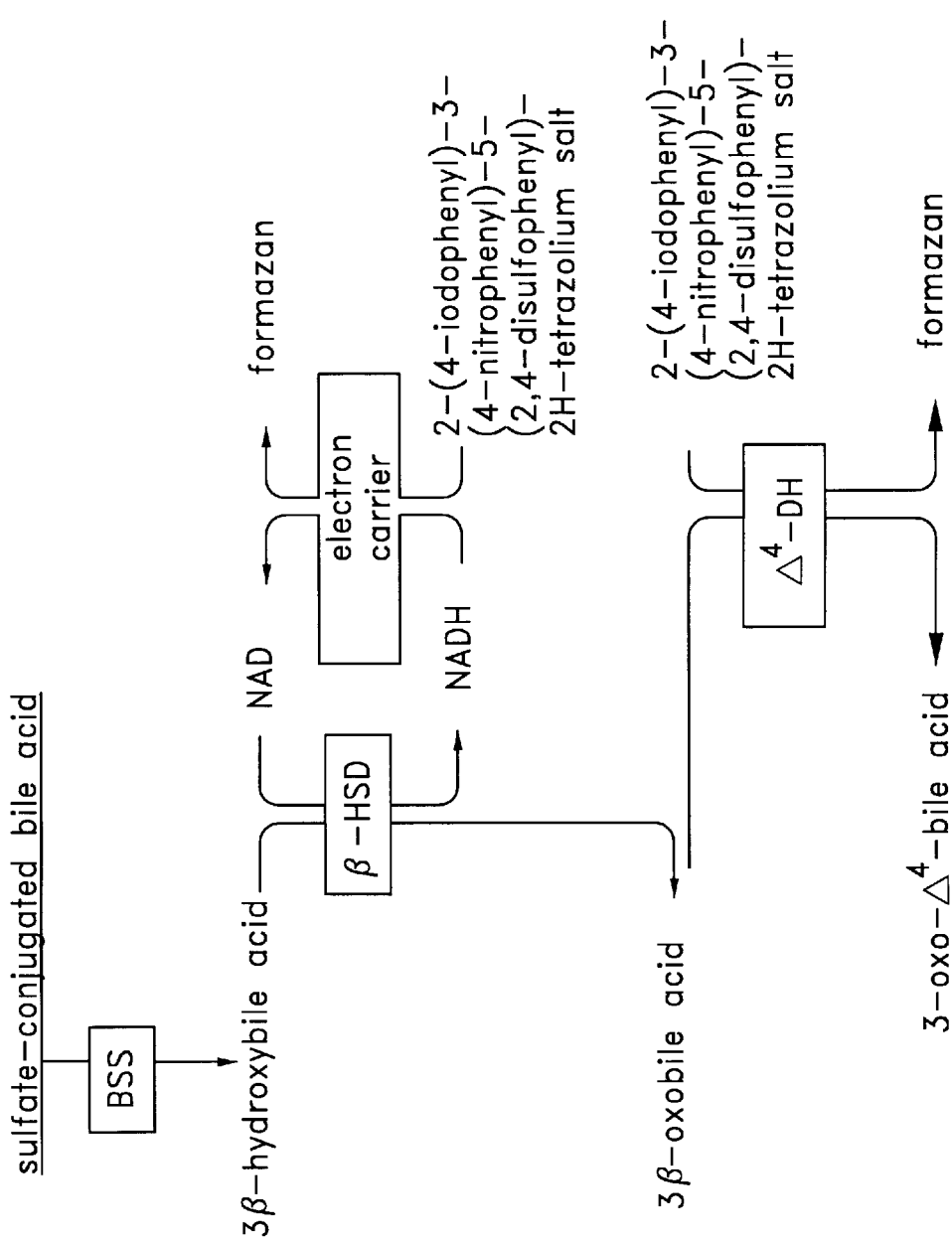
Figure 3:
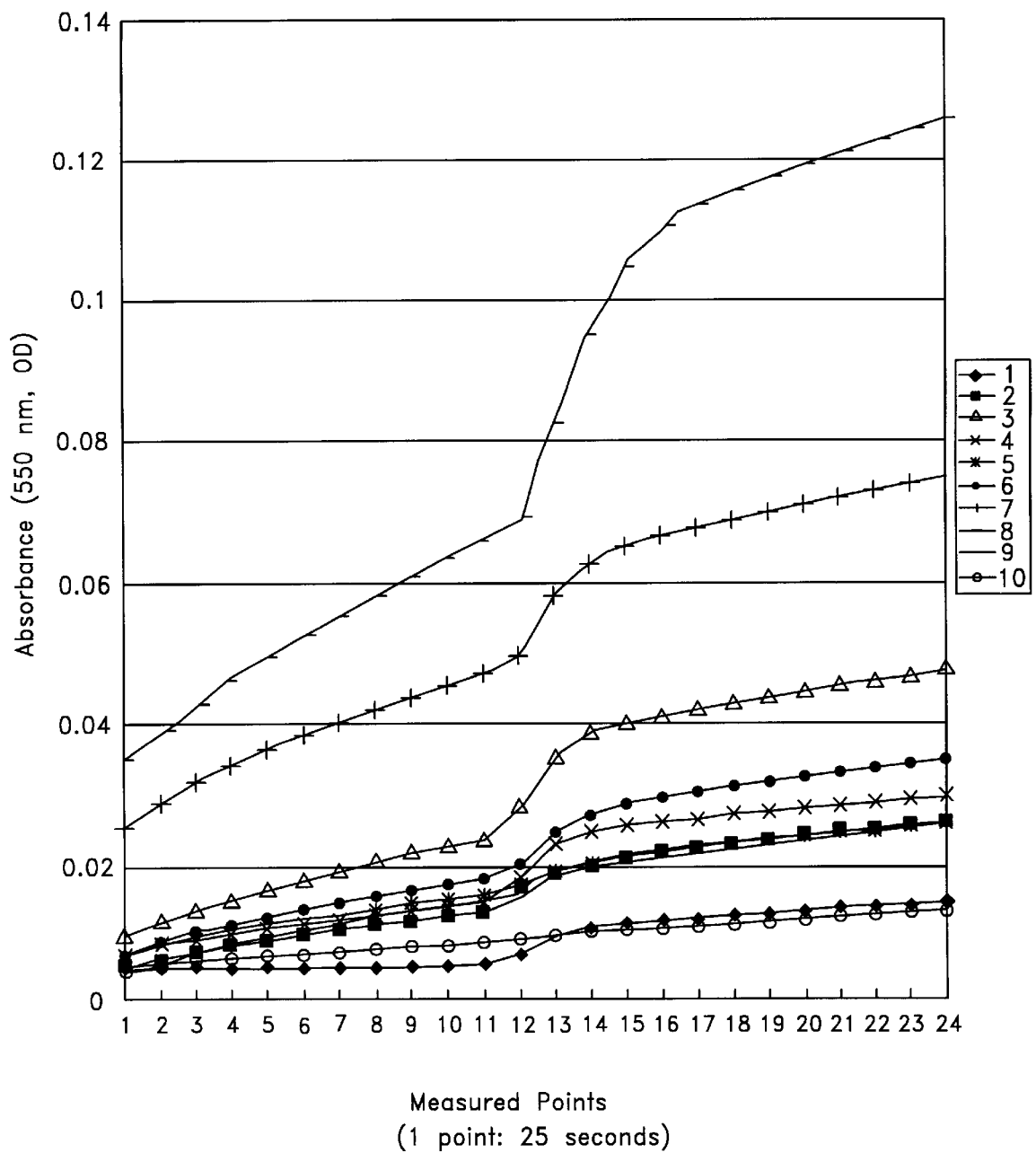
FIG. 3 graphically shows the time courses (1 point: 25 seconds) of absorbance as found by assaying various urine samples (Nos. 1 to 10) on an automated analyzer using NTB as the reductive system indicator.

Time Course of Absorption When Nitrotetrazolium Blue (NTB) (Comparative reagent a) Was Used as Reductive System Indicator Ten urine samples were subjected to assaying on an automated analyzer (COBAS MIRA) using NTB as the reductive system indicator and using the first and the second reagents respectively having the compositions shown below, and the time courses of absorbance of the resulting reaction system were followed. The reaction temperature was 37° C. Following placing 20 μl of the sample, 30 μl of purified water and 160 μl of the first reagent in each cuvette, the reaction was allowed to proceed for 5 minutes. Then, 40 μl of the second reagent and 10 μl of purified water were further added to the cuvette, and the absorbance of the reaction mixture was measured at 550 nm at 25-second intervals. The concentrations of the respective ingredients in the first and the second reagents were as follows:

First reagent (pH 7.5)
  Diaphorase (Oriental Yeast): 5,000 U/L
  β-HSD (purified as described in J. Biol. Chem., 252, 3775–3783 (1977)): 500 U/L
  β-NAD (Oriental Yeast): 1 g/L
  NTB (Nacalai Tesque): 0.5 g/L
  ASOD (Oriental Yeast): 200 U/L
  Tween 20 (Nacalai Tesque): 0.5% by weight
  Sorbitol (Nacalai Tesque): 20% by weight
  HEPES (Nacalai Tesque): 100 mM
Second reagent (pH 7.5)
  BSS (purified as described in Biosci. Biotech. Biochem., 58, 889–894 (1994)): 2,000 U/L
  Tween 20: 0.5% by weight
  Sorbitol: 20% by weight
  HEPES: 100 mM The results are shown in FIG. 3. The blank value in the first reaction increased linearly. The tendency toward increase was not completed within the predetermined period of 5 minutes and still continued after shifting to the second reaction. Furthermore, varieties were observed in the tendency toward increase in blank value among urine samples.

Therefore, when NTB was used as the reductive system indicator, the above blank reaction had to be additionally carried out in parallel with sample reaction, in another cuvette.

EXAMPLE 1

Time Courses of Absorption When Various Tetrazolium Salts Were Used as Reductive System Indicators Changes in absorbance with time were followed using the following tetrazolium salts as reductive system indicators.
Reductive system indicator:
  (Comparative reagent a) NTB (Nacalai Tesque)
  (Comparative reagent d) 3-(4,5-Dimethyl-2-thiazolyl)-2,5-diphenyl-2H-tetrazolium bromide (Sigma Chemical Co.)

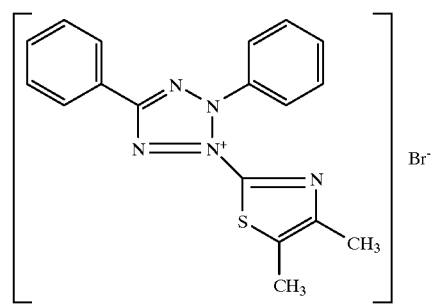

(Comparative reagent b) 2-(4-Iodophenyl)-3-(2,4-dinitrophenyl)-5-(2,4-disulfophenyl)-2H-tetrazolium monosodium salt (Dojindo Laboratories, WST-3) (Comparative reagent c) 2-Benzothiazolyl-3-(4-carboxy-2-methoxyphenyl)-5-[4-(2-sulfoethylcarbamoyl) phenyl]-2H-tetrazolium salt (Dojindo Laboratories, WST-4) (Reductive system indicator of the invention) 2-(4-Iodophenyl)-3-(4-nitrophenyl)-5-(2,4-disulfophenyl)-2H-tetrazolium monosodium salt (Dojindo Laboratories, WST-1)

Figure 4:
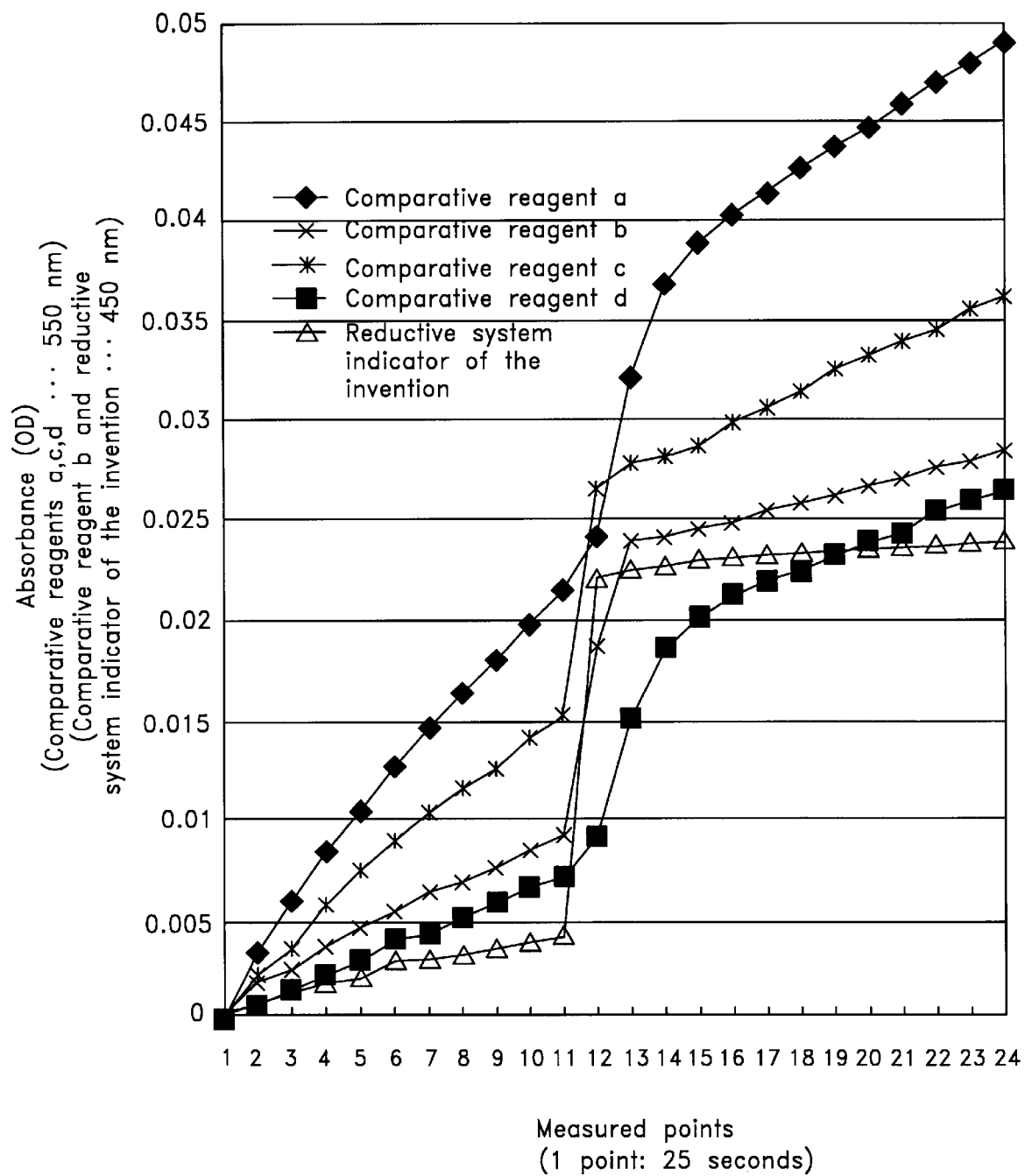
FIG. 4 graphically shows the time courses (1 point: 25 seconds) of absorbance as found by assaying a urine sample on an automated analyzer using different reductive system indicators.

Urine samples were subjected to assaying on an automated analyzer (COBAS MIRA) using the first and the second reagent respectively having the compositions shown below and the time courses of absorbance of the reaction system were followed. The reaction temperature was 37° C. Following placing 20 μl of the sample, 30 μl of purified water and 160 μl of the first reagent in a cuvette, the reaction was allowed to proceed for 5 minutes. Then, 40 μl of the second reagent and 10 μl of purified water were further added to the cuvette, and absorbance of the reaction mixture was measured at 25-second intervals. The absorbance was measured at 550 nm when Comparative reagents a, c and d were used, and at 450 nm when Comparative reagent b and the reductive system indicator of the invention were used. The concentrations of the respective ingredients in the first and the second reagents were as follows:

First reagent (pH 7.5)
  Diaphorase: 5,000 U/L
  β-HSD: 500 U/L
  β-NAD: 1 g/L
  Each reductive system indicator: 0.5 g/L
  ASOD: 200 U/L
  Tween 20: 0.5% by weight
  Sorbitol: 20% by weight
  HEPES: 100 mM
Second reagent (pH 7.5)
  BSS: 2,000 U/L
  Tween 20: 0.5% by weight
  Sorbitol: 20% by weight
  HEPES: 100 mM The results are shown in FIG. 4. While the blank value showed a continued increase with Comparative reagents a, b, c and d, the reductive system indicator of the invention allowed rapid reaction progress, with the blank value stably remaining within tolerance limits without being significantly affected by endogenous color developing substances in urine.

EXAMPLE 2

Figure 5:
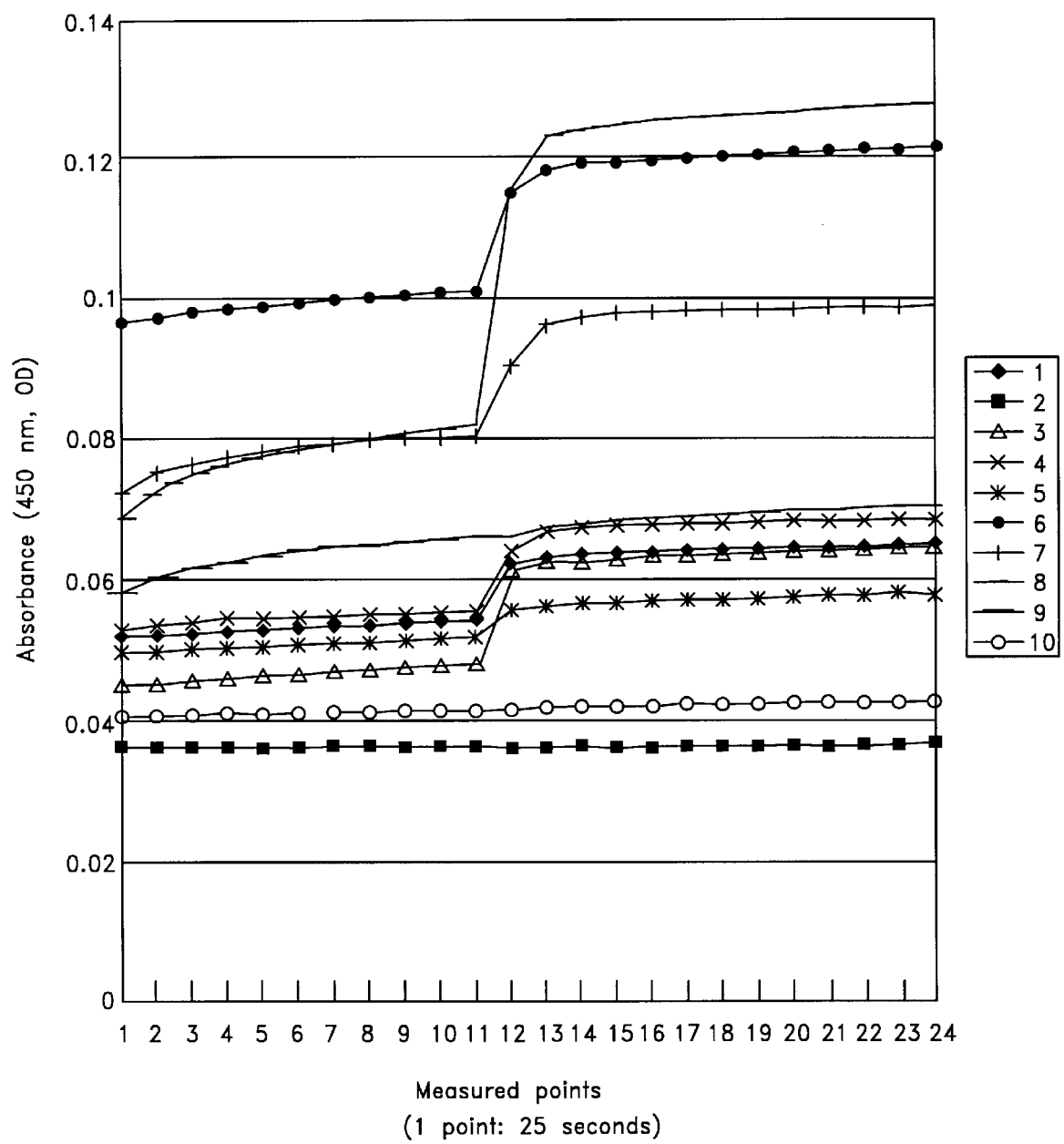
FIG. 5 graphically shows the time courses (1 point: 25 seconds) of absorbance as found by assaying various urine samples (Nos. 1 to 10) on an automated analyzer using the reductive system indicator of the invention.

Time Course of Absorbance When 2-(4-iodophenyl)-3-(4-nitrophenyl)-5-(2,4-disulfophenyl)-2H-tetrazolium Salt (Reductive System Indicator of the Invention) Was Used as Reductive System Indicator With 10 urine samples, the time courses of absorbance were followed in the same manner as in Example 1 using 2-(4-iodophenyl)-3-(4-nitrophenyl)-5-(2,4-disulfophenyl)-2H-tetrazolium monosodium salt (Dojindo Laboratories, WST-1) as the reductive system indicator. The results are shown in FIG. 5.

With each urine sample, the blank value became nearly stabilized within 5 minutes and the reaction proceeded rapidly and, in 2 to 3 minutes after addition of the second reagent, sulfate-conjugated bile acid could be determined under little influence of the variation in blank value.

EXAMPLE 3

Correlationship Between the Prior Art Method and the Method of the Present Invention Urine samples were used and the correlation between the measured values obtained by the method of the present invention and those obtained by the prior art method was examined. In the method of the present invention, NTB (Comparative-reagent a) and 2-(4-iodophenyl)-3-(4-nitrophenyl)-5-(2,4-disulfophenyl)-2H-tetrazolium monosodium salt (reductive system indicator of the invention) respectively were adopted as the reductive system indicator.

Assaying by the prior art method was performed using "UBASTEC" (Marukin Shoyu Co., Ltd.) and, more specifically, as follows.

Test tubes for assaying sample and blank of sample were prepared, and 200 μl of urine was added to each test tube. After addition of 400 μl of the first prime (1') reagent enzyme solution specified below to the test tube for assaying sample and 400 μl of the first prime reagent blank solution specified below to the test tube for assaying blank, and mixing up, the tubes were warmed at 37° C. for 10 minutes. To each test tube was added 500 μl of the second prime (2') color developing solution specified below, followed by further 10 minutes of warming at 37° C. Then, 100 μl of 2M aqueous citric acid solution was added to each test tube to terminate the reaction. The absorbance (A') of the reaction mixture with the first prime reagent enzyme solution added and the absorbance (B') of the reaction mixture with the first prime reagent blank solution added were measured at the wavelength of 540 nm, with water as a control, the difference (A'–B') was calculated, and the concentration of sulfate-conjugated bile acid in each urine sample was determined based on the standard value obtained with a standard solution (glycolithocholic acid-3-sulfate, 50 μmol/L).
First prime (1') reagent enzyme solution
  BSS: 2.5 U/ml
  ASOD: 2.5 U/ml
  Tris-HCl buffer: 0.1M (pH 7.5)
First prime (1') reagent blank solution
  ASOD: 2.5 U/ml
  Tris-HCl buffer: 0.1M (pH 7.5)
Second prime (2') color developing solution
  Diaphorase: 4.0 U/ml
  β-HSD: 0.7 U/ml
  β-NAD: 1.3 mg/ml
  NTB: 0.4 mg/ml
  Phosphate buffer: 0.2M (pH 7.0)
The method of the present invention was carried out as follows.

Figure 6:
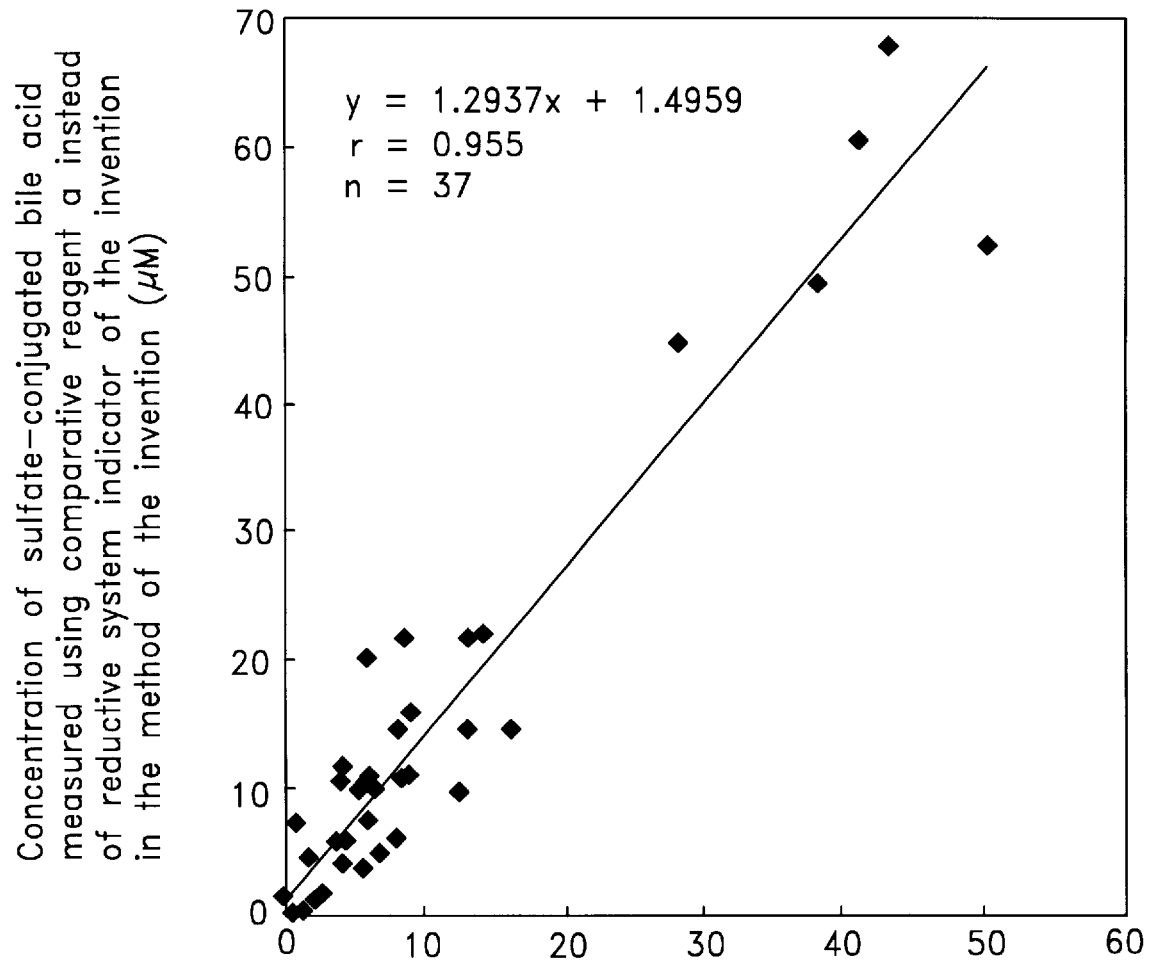
FIG. 6 illustrates the correlationship between the value measured with NTB as the reductive system indicator using an automated analyzer and the corresponding value manually measured by the prior art method.
Figure 7:
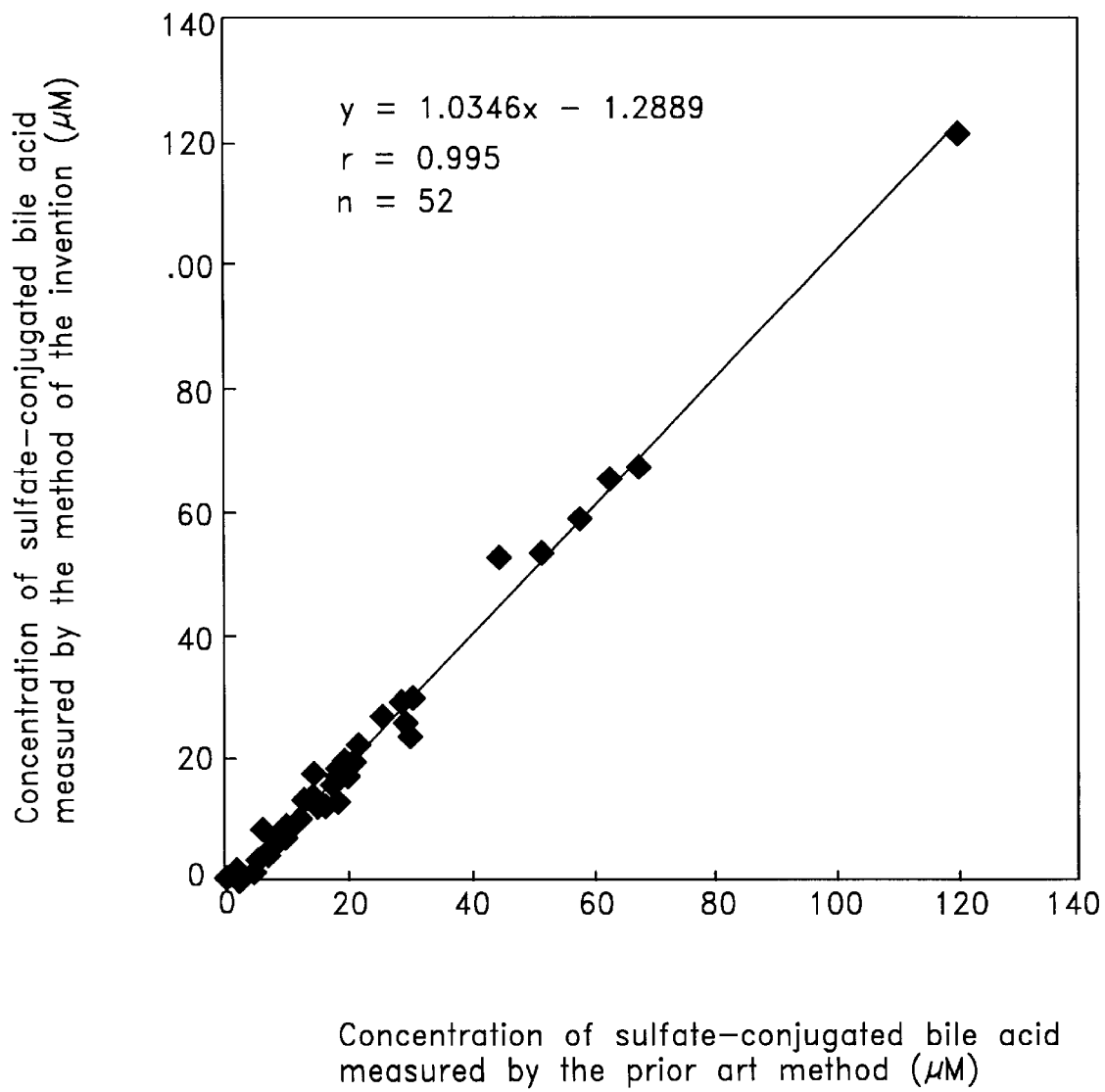
FIG. 7 illustrates the correlationship between the value by measured by the method of the present invention (automated analysis using the reductive system indicator of the invention) and the value manually measured by the prior art method.

Assaying of various urine samples was performed on a Hitachi model 7070 automated analyzer using the first and second reagents with the respective compositions shown below. The reaction temperature was 37° C. Following admixing 20 μl of the sample with 240 μl of the first reagent, the reaction was allowed to proceed for 5 minutes and 50 μl of the second reagent was then added. The difference in absorbance as obtained by subtracting the absorbance value at 450 nm measured before addition of the second reagent (blank value) from the absorbance value at 450 nm measured 2 minutes after addition of the second reagent was employed as the measured value. The concentration of sulfate-conjugated bile acid in each urine sample was determined based on the standard value obtained with a standard solution (glycolithocholic acid-3-sulfate, 50 μmol/L, (Sigma Chemical Co.)).
First reagent (pH 7.5)
  Diaphorase: 5,000 U/L
  β-HSD: 500 U/L
  β-NAD: 1 g/L
  Comparative reagent a or reductive system color former of the invention: 0.5 g/L
  ASOD: 200 U/L
  Tween 20: 0.5% by weight
  Sorbitol: 20% by weight
  HEPES: 100 mM
Second reagent (pH 7.5)
  BSS: 2,000 U/L
  Tween 20: 0.5% by weight
  Sorbitol: 20% by weight
  HEPES: 100 mM The results are shown in FIG. 6 and FIG. 7. With NTB, the measured value was higher (about 1.3-fold) than that of the prior art method because of inclusion of the increment in blank value, hence the coefficient of correlation tended to become worse.

With the reductive system indicator of the invention, on the contrary, the coefficient of correlation with the prior art method was very good (r=0.995) and the relation of each measured value showed a substantially one-to-one, indicating that the method of the present invention is comparable in accuracy to the prior art method.

EXAMPLE 4

Effects of the Present Invention With the First Reagent Containing Diaphorase

Figure 8:
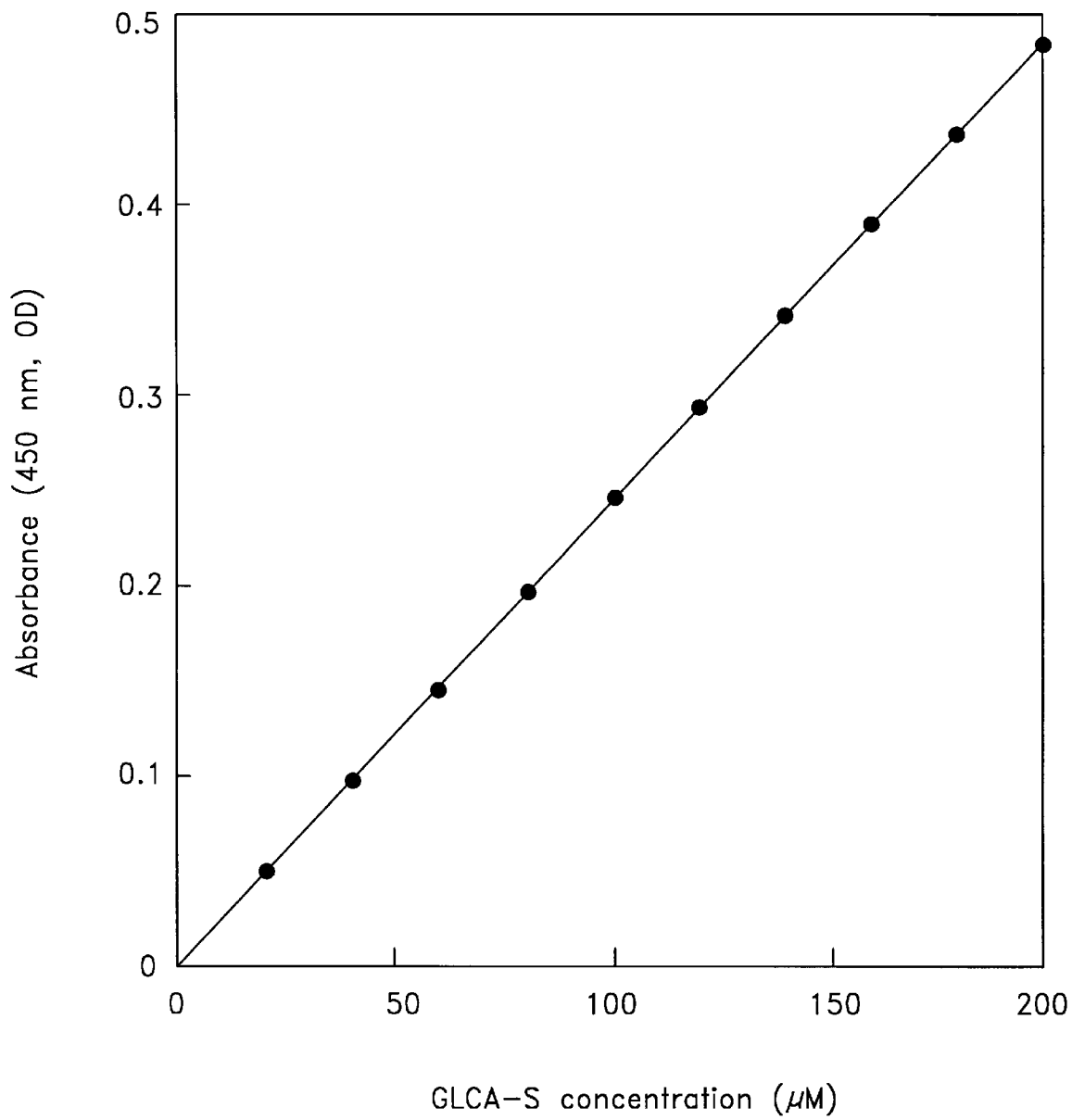
FIG. 8 shows the GLCA-S concentration versus change in absorbance (at 450 nm) data obtained in Example 4.
Figure 9:
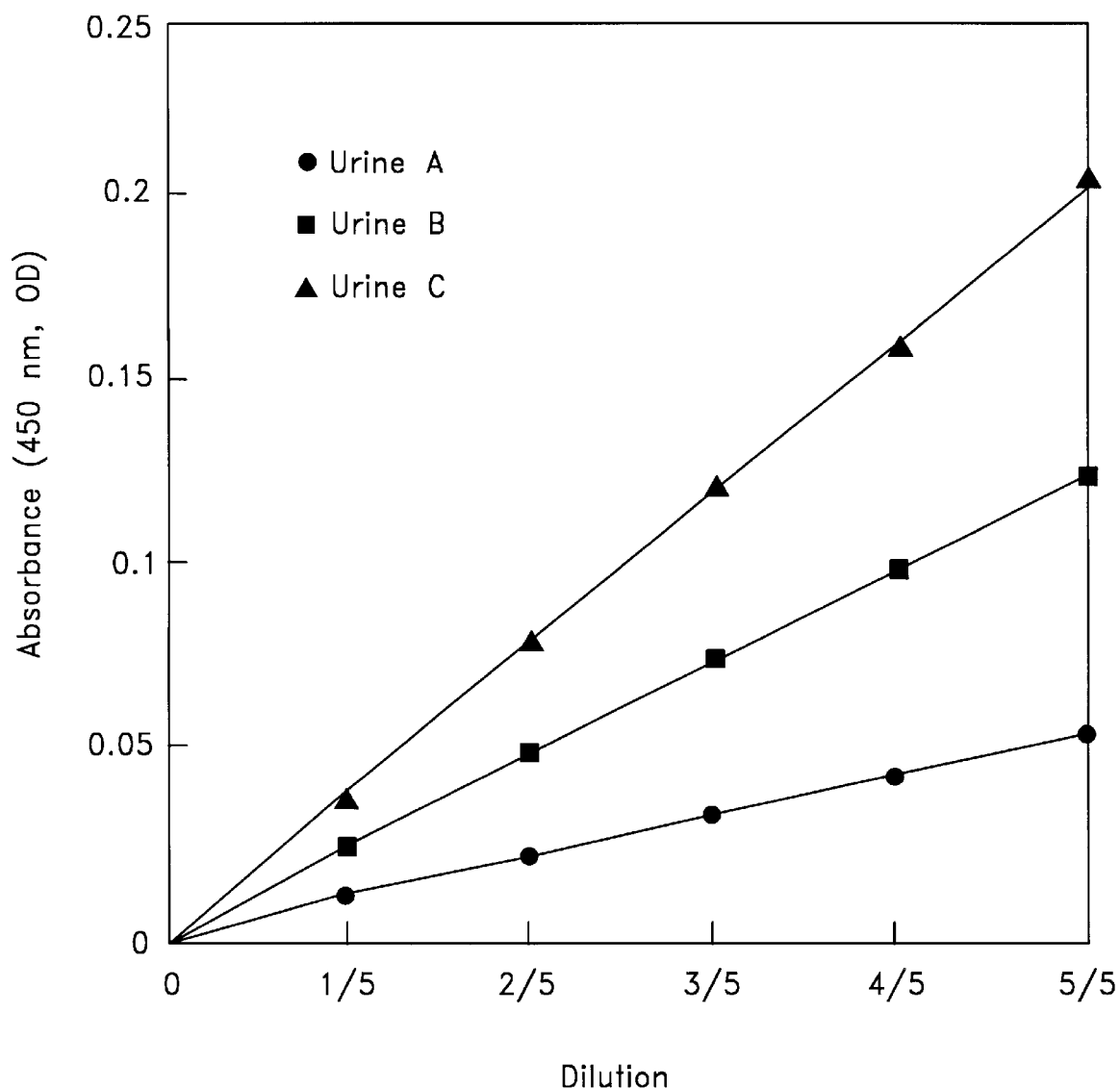
FIG. 9 shows the urinary concentration versus change in absorbance (at 450 nm) data obtained in Example 4.

Glycolithocholic acid-3-sulfate (GLCA-S) solutions having various concentrations (20 to 200 μmol/L) and five serial dilutions each of three urine samples were subjected to assaying on a Hitachi model 7070 automated analyzer using the first and the second reagents having the respective compositions shown below. The reductive system indicator used was 2-(4-iodophenyl)-3-(4-nitrophenyl)-5-(2,4-disulfophenyl)-2H-tetrazolium monosodium salt (reductive system indicator of the invention) described in Example 1. The reaction temperature was 37° C. Following admixing 20 μl of the sample with 240 μl of the first reagent, the reaction was allowed to proceed for 5 minutes and 50 μl of the second reagent was then added. The difference in absorbance as obtained by subtracting the absorbance value at 450 nm measured before addition of the second reagent (blank value) from the absorbance value at 450 nm measured 2 minutes after addition of the second reagent was employed as the measured value.
First reagent (pH 7.5)
  Diaphorase: 5,000 U/L
  β-HSD: 500 U/L β-NAD: 1 g/L
Reductive system indicator of the invention: 0.5 g/L
ASOD: 200 U/L
Tween 20: 0.5% by weight
Sorbitol: 20% by weight
HEPES: 100 mM
Second reagent (pH 7.5)
BSS: 2,000 U/L
Tween 20: 0.5% by weight
Sorbitol: 20% by weight
HEPES: 100 mM The results are shown in FIG. 8 and FIG. 9. As shown in FIG. 8, the relation between the GLCA-S concentration and the measured value was illustrated as a line passing through the origin with excellent linearity. As shown in FIG. 9, results obtained with the 5 serial dilutions of each of the three urine samples were as well.

EXAMPLE 5

Effects of the Present Invention With the First Reagent Containing Diaphorase and $\Delta^4$-DH Glycolithocholic acid-3-sulfate (GLCA-S) solutions having various concentrations (20 to 200 μmol/L) and five serial dilutions each of three urine samples were subjected to assaying on a Hitachi model 7070 automated analyzer using the first and the second reagents having the respective compositions shown below. The reductive system indicator used was 2-(4-iodophenyl)-3-(4-nitrophenyl)-5-(2,4-disulfophenyl)-2H-tetrazolium monosodium salt (reductive system indicator of the invention) described in Example 1. The reaction temperature was 37° C. Following admixing 20 μl of the sample with 240 μl of the first reagent, the reaction was allowed to proceed for 5 minutes and 50 μl of the second reagent was then added. The difference in absorbance as obtained by subtracting the absorbance value at 450 nm measured before addition of the second reagent (blank value) from the absorbance value at 450 nm measured 2 minutes after addition of the second reagent was employed as the measured value.

Figure 10:
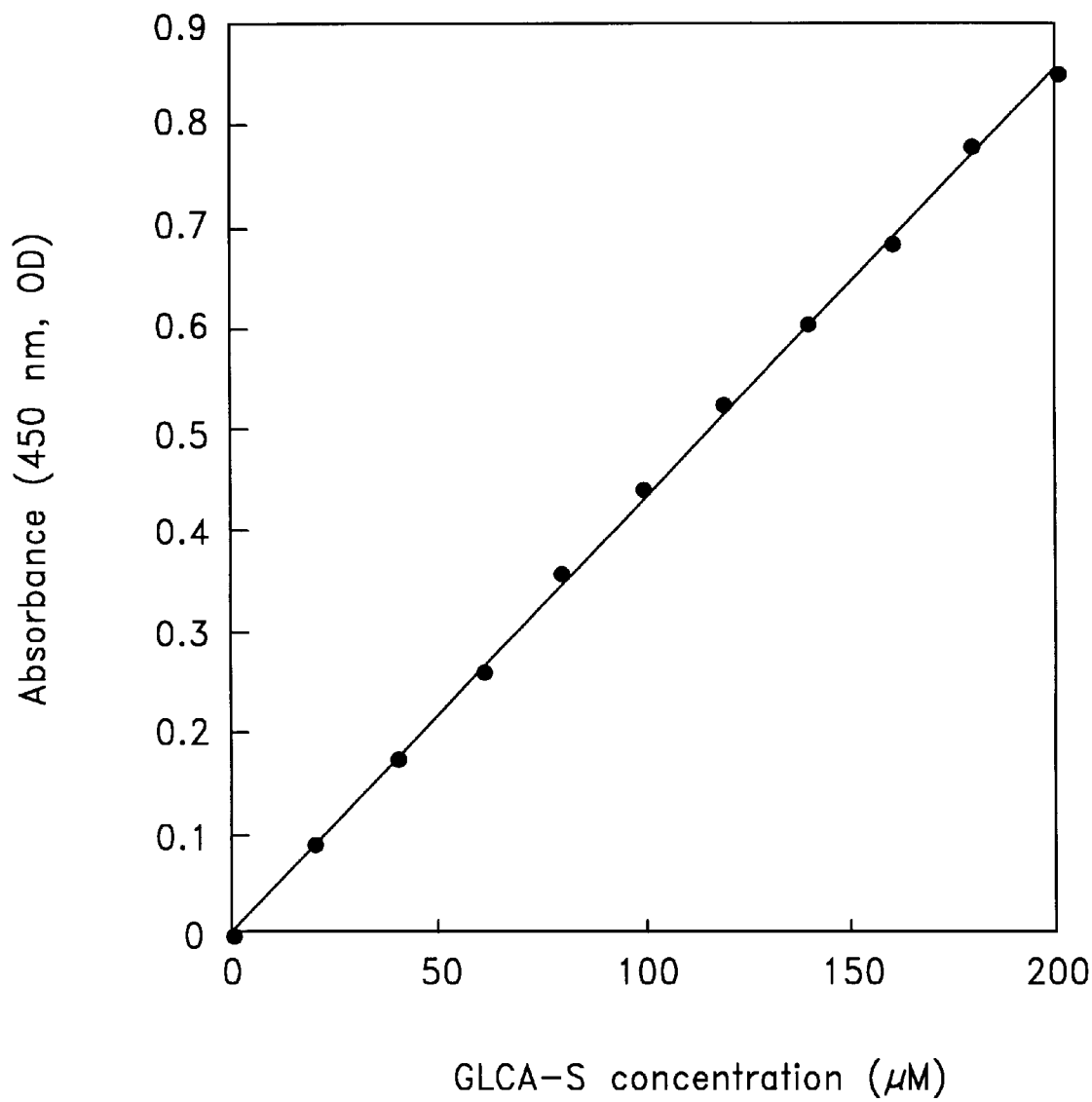
FIG. 10 shows the GLCA-S concentration versus change in absorbance (at 450 nm) data obtained in Example 5.
Figure 11:
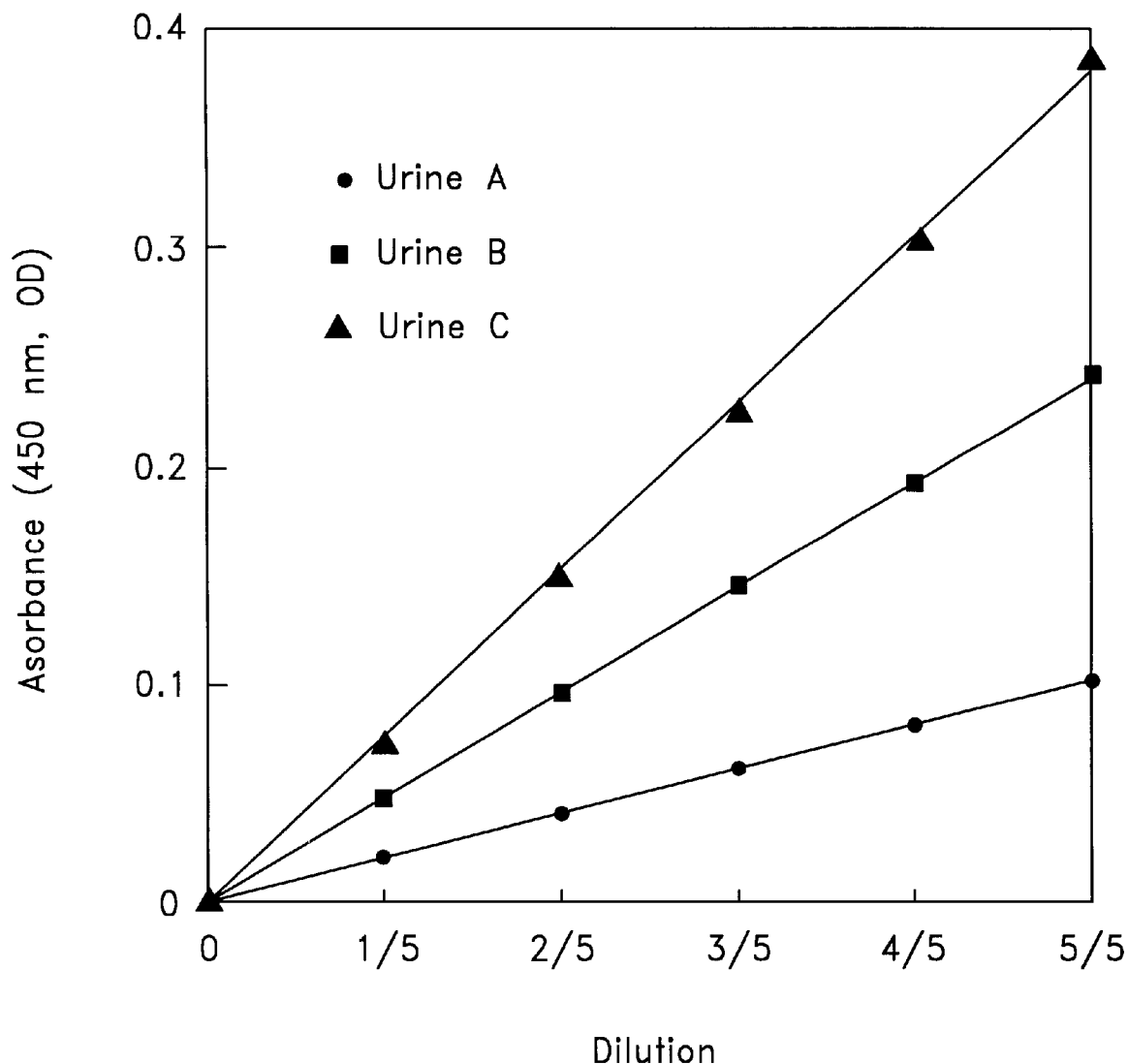
FIG. 11 shows the urinary concentration versus change in absorbance (at 450 nm) data obtained in Example 5.

First reagent (pH 7.5)
Diaphorase: 5,000 U/L
β-HSD: 500 U/L
$\Delta^4$-DH (purified as described in J. Biol. Chem., 241, 906–915 (1966)): 1,000 U/L
β-NAD: 1 g/L
Reductive system indicator of the invention: 0.5 g/L
ASOD: 200 U/L
Tween 20: 0% by weight
Sorbitol: 20% by weight
HEPES: 100 mM
Second reagent (pH 7.5)
BSS: 2,000 U/L
Tween 20: 0.5% by weight
Sorbitol: 20% by weight
HEPES: 100 mM The results are shown in FIG. 10 and FIG. 11. As shown in FIG. 10, the relation between the GLCA-S concentration and the measured value was illustrated as a line-passing through the origin with excellent linearity. As shown in FIG. 11, results obtained with the 5 serial dilutions of each of the three urine samples were as well.

EXAMPLE 6

Effects of the Present Invention With the First Reagent Containing 1-methoxy-PMS Glycolithocholic acid-3-sulfate (GLCA-S) solutions having various concentrations (20 to 200 μmol/L) were subjected to assaying on a Hitachi model 7070 automated analyzer using the first and the second reagent having the respective compositions shown below. The reductive system indicator used was 2-(4-iodophenyl)-3-(4-nitrophenyl)-5-(2,4-disulfophenyl)-2H-tetrazolium monosodium salt (reductive system indicator of the invention) described in Example 1. The reaction temperature was 37° C. Following admixing 20 μl of the sample with 240 μl of the first reagent, the reaction was allowed to proceed for 5 minutes and 50 μl of the second reagent was then added. The difference in absorbance as obtained by subtracting the absorbance value at 450 nm measured before addition of the second reagent (blank value) from the absorbance value at 450 nm measured 2 minutes after addition of the second reagent was employed as the measured value.

Figure 12:
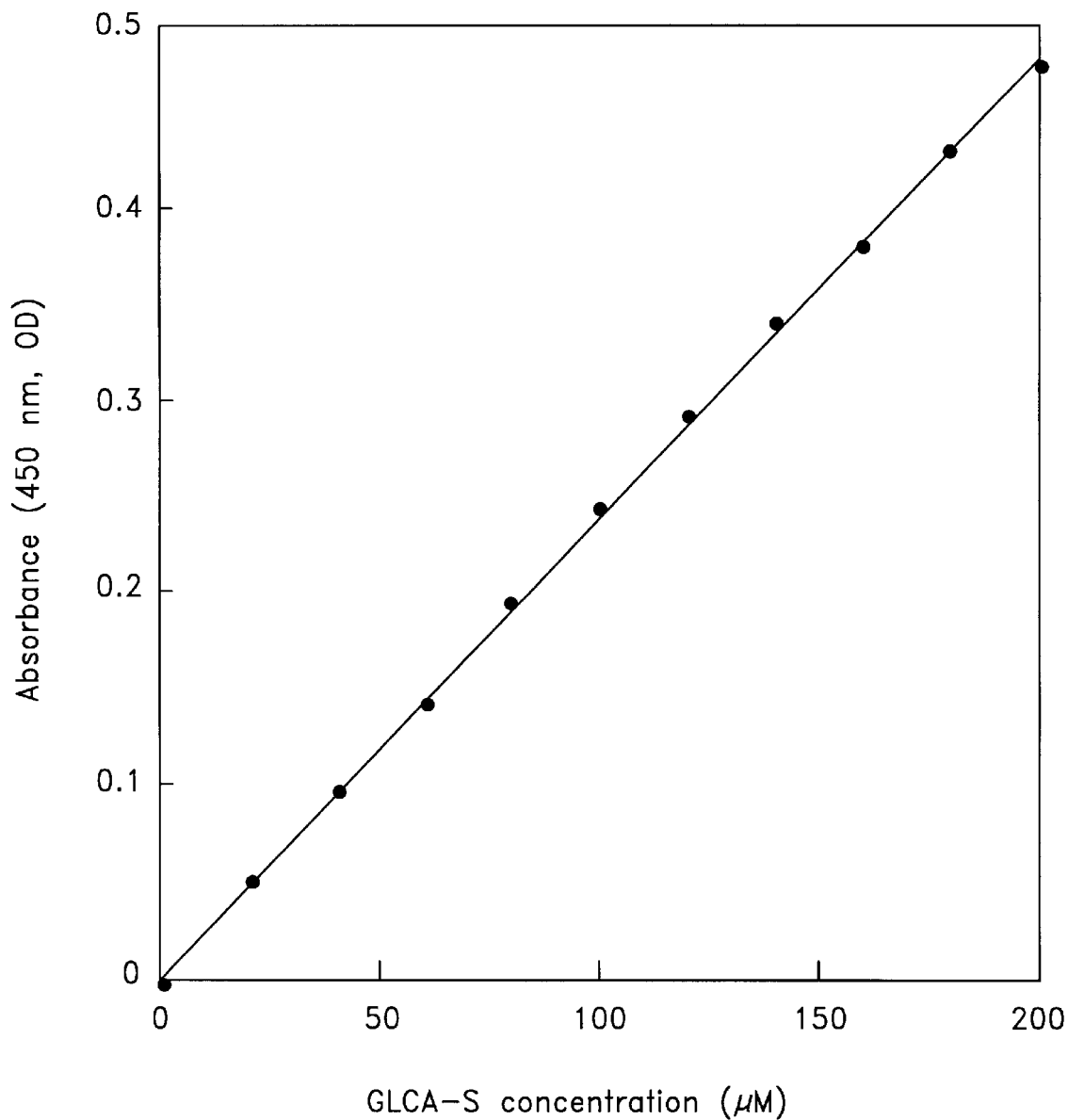
FIG. 12 shows the GLCA-S concentration versus change in absorbance (at 450 nm) data obtained in Example 6.

First reagent (pH 7.5)
1-Methoxy-PMS (Dojindo Laboratories): 0.05 mM
β-HSD: 500 U/L
β-NAD: 1 g/L
Reductive system indicator of the invention: 0.5 g/L
ASOD: 200 U/L
Tween 20: 0.5% by weight
Sorbitol: 20% by weight
HEPES: 100 mM
Second reagent (pH 7.5)
BSS: 2,000 U/L
Tween 20: 0.5% by weight
Sorbitol: 20% by weight
HEPES: 100 mM The results are shown in FIG. 12. As shown in FIG. 12, the relation between the GLCA-S concentration and the measured value was illustrated as a line passing through the origin with excellent linearity.

We claim:

1. In a method of quantifying sulfate-conjugated bile acid in a sample with bile acid sulfate sulfatase and a reductive system indicator, wherein the improvement comprises using an 2-(4-iodophenyl)-3-(4-nitrophenyl)-5-(2,4disulfophenyl)-2H-tetrazolium salt as a reductive system indicator.

2. A method of quantifying sulfate-conjugated bile acid in a sample, which comprises the steps of:
    (1) contacting bile acid sulfate sulfatase with the sample to form 3, β-hydroxybile acid,
    (2) contacting β-hydroxysteroid dehydrogenase with the 3β-hydroxybile acid in the presence of nicotinamide adenine dinucleotide to form NADH and 3-oxobile acid,
    (3) contacting an electron carrier and an 2-(4-iodophenyl)-3-(4-nitrophenyl)-5-(2,4-disulfophenyl)-2H-tetrazolium salt with the NADH to form formazan, followed by quantifying the formazan, and
    (4) determining the quantity of sulfate-conjugated bile acid based on the quantity of the formazan.

3. A method according to claim 2, wherein the electron carrier is at least one member selected from the group consisting of diaphorase, 1-methoxyphenazinium methyl sulfate and 9-dimethylaminobenzo-α-phenazoxonium chloride.

4. A method of quantifying sulfate-conjugated bile acid in a sample, which comprises the steps of:
   (1) contacting bile acid sulfate sulfatase with the sample to form 3β-hydroxybile acid,
   (2) contacting β-hydroxysteroid dehydrogenase with the 3β-hydroxybile acid in the presence of nicotinamide adenine dinucleotide to form NADH and 3-oxobile acid,
   (3) (i) contacting an electron carrier and a 2-(4-iodophenyl)-3-(4-nitrophenyl)-5-(2,4-disulfophenyl)-2H-tetrazolium salt with the NADH to form formazan,
   (ii) contacting 3-oxo-5β-steroid-$\Delta^4$-dehydrogenase and the 2-(4-iodophenyl)-3-(4-nitrophenyl)-5-(2,4-disulfophenyl)-2H-tetrazolium salt with said 3-oxobile acid to form formazan, and
   (iii) determining the quantity of sulfate-conjugated bile acid in the sample based on the total quantity of the formazan formed in step (i) and the formazan formed in step (ii).

5. A method according to claim 4, wherein the electron carrier is at least one member selected from the group consisting of diaphorase, 1-methoxyphenazinium methyl sulfate and 9-dimethylaminobenzo-α-phenazoxonium chloride.

6. A kit for quantifying sulfate conjugated bile acid in a sample, which comprises:
   a first reagent comprising β-hydroxysteroid dehydrogenase, nicotinamide adenine dinucleotide, an electron carrier and an 2-(4-iodophenyl)-3-(4-nitrophenyl)-5-(2,4-disulfophenyl)-2H-tetrazolium salt; and
   a second reagent comprising bile acid sulfate sulfatase.

7. A kit according to claim 6, wherein the first reagent further comprises 3-oxo-5β-steroid-$\Delta^4$-dehydrogenase.

8. A kit according to claim 7, wherein the electron carrier is at least one member selected from the group consisting of diaphorase, 1-methoxyphenazinium methyl sulfate and 9-dimethylaminobenzo-α-phenazoxonium chloride.

9. A kit according to claim 6, wherein the electron carrier is at least one member selected from the group consisting of diaphorase, 1-methoxyphenazinium methyl sulfate and 9-dimethylaminobenzo-α-phenazoxonium chloride.

10. A method of quantifying sulfate-conjugated bile acid in a sample, which comprises the steps of:
   reacting a first reagent with sulfate-conjugated bile acid in the sample, if any, to form a first reaction product, said first reagent comprising β-hydroxysteroid dehydrogenase, nicotinamide adenine dinucleotide, an electron carrier, and a 2-(4-iodophenyl)-3-(4-nitrophenyl)-5-(2,4-disulfophenyl)-2H-tetrazolium salt;
   measuring color development #1 of the first reaction product;
   reacting a second reagent with the first reaction product, if any, to form a second reaction product, said second reagent comprising bile acid sulfate sulfatase;
   measuring color development #2 of the second reaction product;
   comparing color development #1 and color development #2; and
   determining the quantity of sulfate-conjugated bile acid in the sample based on the difference between color development #1 and second color development #2.

* * * * *

UNITED STATES PATENT AND TRADEMARK OFFICE
CERTIFICATE OF CORRECTION

PATENT NO. : 5,919,644
DATED : July 6, 1999
INVENTOR(S) : Kenichi Adachi, Yasuhiko Tazuke and Yoji Tsukada It is certified that error appears in the above-identified patent and that said Letters Patent is hereby corrected as shown below:

On the title page, item [54] and Column 1, line 1, the title of invention, change "METHOD FOR ASSAYING SULFATE-CONJUGATED BILE ACID AND THEREFORE" to --METHOD FOR ASSAYING SULFATE CONJUGATED BILE ACID--.

Signed and Sealed this

Fourth Day of January, 2000

Attest:

*Attesting Officer*

*Acting Commissioner of Patents and Trademarks*